United States Patent
Moore

(10) Patent No.: US 12,004,716 B2
(45) Date of Patent: *Jun. 11, 2024

(54) RELAY LENS SYSTEM FOR BROADBAND IMAGING

(71) Applicant: Stryker Corporation, Kalamazoo, MI (US)

(72) Inventor: Frederick Allen Moore, Vancouver (CA)

(73) Assignee: Stryker Corporation, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/657,738

(22) Filed: Apr. 1, 2022

(65) Prior Publication Data

US 2022/0218179 A1    Jul. 14, 2022

Related U.S. Application Data

(63) Continuation of application No. 14/636,448, filed on Mar. 3, 2015, now Pat. No. 11,304,592.

(60) Provisional application No. 62/084,292, filed on Nov. 25, 2014, provisional application No. 61/947,776, filed on Mar. 4, 2014.

(51) Int. Cl.
| | | |
|---|---|---|
| A61B 1/002 | (2006.01) | |
| A61B 1/055 | (2006.01) | |
| G02B 13/00 | (2006.01) | |
| G02B 23/24 | (2006.01) | |
| G02B 27/00 | (2006.01) | |
| H04N 23/00 | (2023.01) | |
| H04N 23/50 | (2023.01) | |

(52) U.S. Cl.
CPC .............. *A61B 1/002* (2013.01); *A61B 1/055* (2013.01); *G02B 13/0095* (2013.01); *G02B 23/2446* (2013.01); *G02B 27/0062* (2013.01); *H04N 23/00* (2023.01); *H04N 23/555* (2023.01)

(58) Field of Classification Search
CPC ........ A61B 1/002; A61B 1/055; H04N 5/225; G02B 23/2446; G02B 27/0062; G02B 13/0095

See application file for complete search history.

(56) References Cited

U.S. PATENT DOCUMENTS

| | | | |
|---|---|---|---|
| 4,693,568 | A | 9/1987 | Takahashi |
| 4,783,152 | A | 11/1988 | Nishimoto |
| 4,981,342 | A | 1/1991 | Fiala |
| 5,206,759 | A | 4/1993 | Ono et al. |
| 5,212,589 | A | 5/1993 | Goodman |

(Continued)

FOREIGN PATENT DOCUMENTS

| | | |
|---|---|---|
| CH | 694174 A5 | 8/2004 |
| CN | 1230115 C | 12/2005 |

(Continued)

OTHER PUBLICATIONS

US 6,692,429 B1, 02/2004, Imaizumi et al. (withdrawn)

(Continued)

*Primary Examiner* — Shawn S An
(74) *Attorney, Agent, or Firm* — Morrison & Foerster LLP

(57) ABSTRACT

An optical system includes a first relay rod of a first material, a second relay rod of a second material, different from the first material, and a lens between the first and second relay rods.

14 Claims, 5 Drawing Sheets

(56) References Cited

U.S. PATENT DOCUMENTS

| | | | |
|---|---|---|---|
| 5,276,321 A | 1/1994 | Chang et al. | |
| 5,296,971 A | 3/1994 | Mori | |
| 5,341,240 A | 8/1994 | Broome | |
| 5,457,576 A * | 10/1995 | Atkinson | G02B 27/0037 359/435 |
| 5,561,525 A | 10/1996 | Toyonaga et al. | |
| 5,633,754 A | 5/1997 | Hoogland | |
| 5,646,730 A | 7/1997 | Mitchell et al. | |
| 5,684,629 A * | 11/1997 | Leiner | G02B 13/0095 359/434 |
| 5,790,314 A * | 8/1998 | Duck | G02B 6/2937 385/33 |
| 5,822,128 A | 10/1998 | Sekine | |
| 5,825,534 A | 10/1998 | Strähle | |
| 5,867,315 A | 2/1999 | Koike et al. | |
| 6,049,422 A | 4/2000 | Ibe | |
| 6,141,159 A * | 10/2000 | Nishio | G02B 27/0037 359/717 |
| 6,269,057 B1 | 7/2001 | McDonald et al. | |
| 6,301,043 B1 | 10/2001 | Ducket, III | |
| 6,438,290 B1 * | 8/2002 | Bietry | G02B 3/04 385/33 |
| 6,485,413 B1 * | 11/2002 | Boppart | A61B 1/07 600/478 |
| 6,665,556 B1 * | 12/2003 | Alfano | A61B 5/0084 600/476 |
| 6,734,966 B2 | 5/2004 | McCarthy | |
| 6,747,280 B1 | 6/2004 | Weiss | |
| 6,817,975 B1 | 11/2004 | Farr et al. | |
| 7,057,647 B1 | 6/2006 | Monroe | |
| 7,085,076 B2 | 8/2006 | Sallander | |
| 7,132,654 B2 | 11/2006 | Moisel | |
| 7,180,673 B2 | 2/2007 | Dowski | |
| 7,230,756 B2 | 6/2007 | Hoogland | |
| 7,315,357 B2 | 1/2008 | Ortyn et al. | |
| 7,466,495 B2 | 12/2008 | Kuroda et al. | |
| 7,495,833 B2 | 2/2009 | Powell et al. | |
| 7,518,726 B2 | 4/2009 | Rulison et al. | |
| 7,728,975 B1 | 6/2010 | Totzeck et al. | |
| 7,733,584 B2 | 6/2010 | Kazakevich | |
| 8,619,184 B2 | 12/2013 | Podoleanu | |
| 9,176,069 B2 | 11/2015 | Sullivan et al. | |
| 9,547,178 B2 | 1/2017 | Erdogan et al. | |
| 9,578,252 B2 | 2/2017 | Laroia | |
| 9,648,254 B2 | 5/2017 | Darty et al. | |
| 10,656,316 B2 | 5/2020 | Moore | |
| 10,948,638 B2 | 3/2021 | Moore | |
| 11,304,592 B2 * | 4/2022 | Moore | G02B 13/0095 |
| 2002/0080501 A1 | 6/2002 | Kawae et al. | |
| 2003/0086171 A1 * | 5/2003 | McGuire | G03F 7/70216 359/489.15 |
| 2003/0228053 A1 | 12/2003 | Li et al. | |
| 2004/0114495 A1 * | 6/2004 | Kim | G11B 7/0956 |
| 2004/0186351 A1 | 9/2004 | Imaizumi et al. | |
| 2004/0190762 A1 | 9/2004 | Dowski et al. | |
| 2004/0228005 A1 | 11/2004 | Dowski et al. | |
| 2005/0018312 A1 | 1/2005 | Gruner et al. | |
| 2005/0088730 A1 | 4/2005 | Sangu et al. | |
| 2005/0119529 A1 * | 6/2005 | Farr | G02B 25/001 600/160 |
| 2005/0146634 A1 | 7/2005 | Silverstein et al. | |
| 2005/0146720 A1 | 7/2005 | Hansen et al. | |
| 2005/0171079 A1 | 8/2005 | Schrimpf et al. | |
| 2005/0182321 A1 | 8/2005 | Frangioni | |
| 2005/0275956 A1 | 12/2005 | Larson et al. | |
| 2006/0018234 A1 | 1/2006 | Sugi et al. | |
| 2006/0204204 A1 | 9/2006 | Zenzinger et al. | |
| 2006/0221475 A1 | 10/2006 | Liu | |
| 2007/0012704 A1 | 1/2007 | Grinnall et al. | |
| 2007/0035852 A1 | 2/2007 | Farr | |
| 2007/0081166 A1 | 4/2007 | Brown et al. | |
| 2007/0093993 A1 * | 4/2007 | Stork | H04N 23/00 703/2 |
| 2007/0159701 A1 | 7/2007 | Campbell et al. | |
| 2007/0242327 A1 | 10/2007 | Powell et al. | |
| 2007/0268575 A1 | 11/2007 | Yamazaki | |
| 2007/0279637 A1 * | 12/2007 | Hill | G03F 1/78 356/486 |
| 2008/0049314 A1 | 2/2008 | Steffen et al. | |
| 2008/0273247 A1 | 11/2008 | Kazakevich | |
| 2009/0103792 A1 | 4/2009 | Rahn et al. | |
| 2009/0135612 A1 * | 5/2009 | Maxik | F21V 17/12 362/372 |
| 2009/0261175 A1 | 10/2009 | Kauppinen et al. | |
| 2009/0290236 A1 | 11/2009 | Wang et al. | |
| 2009/0303317 A1 | 12/2009 | Tesar | |
| 2010/0079884 A1 | 4/2010 | Gere | |
| 2010/0262017 A1 | 10/2010 | Frangioni et al. | |
| 2011/0147615 A1 | 6/2011 | Kintz | |
| 2011/0205651 A1 | 8/2011 | Yamano et al. | |
| 2011/0261175 A1 | 10/2011 | Fomitchov et al. | |
| 2011/0316982 A1 | 12/2011 | Johannes et al. | |
| 2012/0154932 A1 | 6/2012 | Katahira et al. | |
| 2012/0320164 A1 | 12/2012 | Lipton | |
| 2013/0083386 A1 | 4/2013 | Harding et al. | |
| 2013/0194667 A1 | 8/2013 | Inoue | |
| 2013/0253273 A1 * | 9/2013 | Duckett, III | A61B 1/002 600/163 |
| 2013/0278747 A1 | 10/2013 | Yang | |
| 2013/0306880 A1 | 11/2013 | Yamano et al. | |
| 2013/0314589 A1 | 11/2013 | Takemoto et al. | |
| 2013/0329094 A1 * | 12/2013 | Ranalli | G06T 5/50 348/241 |
| 2014/0347646 A1 | 11/2014 | Dmitriev et al. | |
| 2015/0029389 A1 | 1/2015 | Masanori | |
| 2015/0256721 A1 | 9/2015 | Moore | |
| 2015/0260652 A1 | 9/2015 | Verstegen et al. | |
| 2015/0309225 A1 | 10/2015 | Moore | |
| 2016/0291332 A1 | 10/2016 | Moore | |
| 2016/0377782 A1 | 12/2016 | Hague | |
| 2021/0239891 A1 | 8/2021 | Moore | |

FOREIGN PATENT DOCUMENTS

| | | |
|---|---|---|
| CN | 101238397 A | 8/2008 |
| CN | 101663576 A | 3/2010 |
| CN | 101950041 A | 1/2011 |
| CN | 103033942 A | 4/2013 |
| DE | 2153198 A1 | 5/1973 |
| EP | 0 646 821 A2 | 4/1995 |
| EP | 2 666 402 A1 | 11/2003 |
| EP | 1 582 894 A1 | 10/2005 |
| EP | 1 607 771 B1 | 12/2005 |
| EP | 1 720 050 A1 | 11/2006 |
| EP | 1 668 420 B1 | 5/2008 |
| EP | 1 777 942 A3 | 2/2010 |
| GB | 2495198 A | 4/2013 |
| JP | H1-284225 A | 11/1989 |
| JP | H2-119108 A | 5/1990 |
| JP | H7-5378 A | 1/1995 |
| JP | H8-54515 A | 2/1996 |
| JP | H8-182653 A | 7/1996 |
| JP | H8-186830 A | 7/1996 |
| JP | H9-43401 A | 2/1997 |
| JP | H9-224903 A | 9/1997 |
| JP | H10-73762 A | 3/1998 |
| JP | H10-115788 A | 5/1998 |
| JP | H10-151104 A | 6/1998 |
| JP | H10-276947 A | 10/1998 |
| JP | H11-281887 A | 10/1999 |
| JP | 2011-28927 A | 5/2001 |
| JP | 2002-532748 A | 10/2002 |
| JP | 2002-369223 A | 12/2002 |
| JP | 2003-18445 A | 1/2003 |
| JP | 2003-98570 A | 4/2003 |
| JP | 2003-524204 A | 8/2003 |
| JP | 2004-47737 A | 2/2004 |
| JP | 2006-165826 A | 6/2006 |
| JP | 2006-267391 A | 10/2006 |
| JP | 2006-285214 A | 10/2006 |
| JP | 2007-52441 A | 3/2007 |
| JP | 2007-515768 A | 6/2007 |

(56) References Cited

FOREIGN PATENT DOCUMENTS

| JP | 2008-545165 | A | 12/2008 |
|---|---|---|---|
| JP | 2010-160312 | A | 7/2010 |
| JP | 2010-526342 | A | 7/2010 |
| JP | 2011-196873 | A | 10/2011 |
| JP | 2013-172967 | A | 9/2013 |
| JP | 2015-7777 | A | 1/2015 |
| KR | 10-2006-0053961 | A | 5/2016 |
| WO | WO-99/019752 | A1 | 4/1999 |
| WO | WO-02/001934 | A2 | 1/2002 |
| WO | WO-2007/020561 | A1 | 2/2007 |
| WO | WO-2010/111649 | A1 | 9/2010 |
| WO | WO-2011/007461 | A1 | 1/2011 |
| WO | WO-2011/120688 | A1 | 10/2011 |
| WO | WO-2012/098806 | A1 | 7/2012 |
| WO | WO-2013/021704 | A1 | 2/2013 |
| WO | WO-2013/119992 | A1 | 8/2013 |
| WO | WO-2015/131278 | A1 | 9/2015 |
| WO | WO-2017/035646 | A1 | 3/2017 |

OTHER PUBLICATIONS

Examination Report No. 1 dated Mar. 27, 2020, directed to AU Application No. 2019204366; 3 pages.
Examination Report No. 1 dated Jun. 21, 2018, directed to AU Application No. 2016314795; 3 pages.
Examination Report No. 2 dated Jun. 15, 2019, directed to AU Application No. 2016314795; 4 pages.
Search Report and Written Opinion dated May 20, 2020, directed to BR Application No. BR112018003903-9; 4 pages.
Office Action dated Mar. 13, 2020, directed to CA Application No. 3,030,495; 4 pages.
Office Action dated May 1, 2020, directed to CA Application No. 3,030,495; 5 pages.
Office Action dated Apr. 28, 2020, directed to CA Application No. 3,047,435; 4 pages.
Notice of Allowance dated Aug. 26, 2019, directed to CA Application No. 2,981,353; 1 page.
Notice of Allowance dated Aug. 27, 2019, directed to CA Application No. 2,941,274; 1 page.
Notice of Allowance dated May 21, 2019, directed to CA Application No. 3,028,775; 1 page.
Notice of Allowance dated Jun. 26, 2019, directed to CA Application No. 2,941,273; 1 page.
Office Action dated Jul. 11, 2017, directed to CA Application No. 2,941,273; 3 pages.
Office Action dated Jul. 12, 2017, directed to CA Application No. 2,941,274; 4 pages.
Office Action dated Jul. 16, 2018, directed to CA Application No. 2,981,353; 4 pages.
Office Action dated Jul. 3, 2018, directed to CA Application No. 2,941,274; 4 pages.
Office Action dated Jun. 21, 2018, directed to CA Application No. 2,941,273; 3 pages.
First Office Action dated Mar. 9, 2020, directed to CN Application No. 201680063915.4; 23 pages.
First Office Action dated May 30, 2018, directed to CN Application No. 201580021609.X; 27 pages.
Second Office Action dated May 7, 2019, directed to CN Application No. 201580021609.X; 7 pages.
Reexamination Notification dated Feb. 21, 2022, directed to CN Application No. 201580021609.X; 17 pages.
Notification to Grant Patent Right for Invention dated Jul. 12, 2022, directed to CN Application No. 201580021609.X; 7 pages.
Notice of Allowance dated Mar. 16, 2020, directed to CN Application No. 201680031742.8, filed Mar. 3, 2015, seven pages.
Notice of Allowance dated Mar. 4, 2020, directed to CN Application No. 201580022991.6; 4 pages.
First Office Action dated Mar. 21, 2019, directed to CN Application No. 2016800317428; 22 pages.

Second Office Action dated Jan. 8, 2019 directed to CN Application No. 201580022991.6; 16 pages.
First Office Action dated Jun. 22, 2018, directed to CN Application No. 201580022991.6; 24 pages.
Third Office Action dated May 10, 2019, directed to CN Application No. 201580022991.6; 9 pages.
Fourth Office Action dated Sep. 26, 2019, directed to CN Application No. 201580022991.6; 10 pages.
Second Office Action dated Sep. 30, 2019, directed to CN Application No. 201680031742.8; 21 pages.
Third Office Action dated Feb. 3, 2020, directed to CN Application No. 201580021609.X; 15 pages.
Second Office Action dated Nov. 13, 2020, directed to CN Application No. 201680063915.4; 7 pages.
Notification to Grant Patent Right for Invention dated Jul. 8, 2021, directed to CN Application No. 201680063915.4; 5 pages.
Decision on Rejection dated Sep. 2, 2020, directed to CN Application No. 201580021609.X; 16 pages.
European Communication Pursuant to Article 94(3) EPC dated Apr. 21, 2020, directed to EP Application No. 16840465.5; 7 pages.
European Communication Pursuant to Rules 70(2) and 70a(2) EPC dated Aug. 18, 2017, directed to EP Application No. 15758117.4; 1 page.
Office Action dated Jul. 29, 2019, directed to EP Application No. 16 771 140.7; 5 pages.
Office Action dated Mar. 5, 2020, directed to EP Application No. 16 771 140.7; 4 pages.
Office Action dated Nov. 23, 2018, directed to EP Application No. 15 758 117.4; 4 pages.
Office Action dated Dec. 20, 2018, directed to EP Application No. 15 758 256.0; 5 pages.
Office Action dated Oct. 11, 2019, directed to EP Application No. 15 758 256.0; 5 pages.
Office Action dated Jun. 9, 2020, directed to EP Application No. 15 758 256.0; 5 pages.
Intention to Grant dated Apr. 26, 2021, directed to EP Application No. 15 758 256.0; 7 pages.
Office Action dated Sep. 18, 2019, directed to EP Patent Application No. 15 758 117.4; 4 pages.
Extended European Search Report dated Aug. 21, 2018, directed to EP Application No. 167711407; 8 pages.
Extended European Search Report dated Mar. 8, 2019, directed to EP Application No. 16840465.5; 8 pages.
Extended European Search Report dated Aug. 12, 2022, directed to EP Application No. 22156337.2; 10 pages.
Summons to Attend Oral Proceedings dated May 25, 2022, directed to EP Application No. 16 840 465.5; 9 pages.
Extended European Search Report dated Jul. 31, 2017, directed to EP Application No. 15758117.4; 8 pages.
Extended European Search Report dated Sep. 11, 2017, directed to EP Application No. 15758256.0; 10 pages.
Intention to Grant dated Nov. 11, 2020, directed to EP Application No. 15 758 117.4, 7 pages.
Extended European Search Report dated Sep. 15, 2021, directed to EP Application No. 21170102.4; 6 pages.
Gross. H et al. (ed.) (Jan. 1, 2007). "Handbook of Optical Systems,— Aberration Theory and Correction of Optical Systems," in Handbook Of Optical Systems, Aberration Theory and Correction of Optical Systems, Wiley-VCH, Weinheim, 3:377-379.
Office Action dated Mar. 27, 2019, directed to IN Application No. 201617030105; 7 pages.
Office Action dated May 17, 2019, directed to IN Application No. 201617030106; 6 pages.
International Preliminary Report on Patentability dated Mar. 15, 2018, directed to International Application No. PCT/CA2016/051023; 6 pages.
International Preliminary Report on Patentability dated Oct. 12, 2017, directed to International Application No. PCT/CA2016/050365; 7 pages.
International Search Report dated May 13, 2015, directed to International Application No. PCT/CA2015/050162; 4 pages.

(56) References Cited

OTHER PUBLICATIONS

International Preliminary Report on Patentability dated Sep. 15, 2016, directed to International Application No. PCT/CA2015/050162; 6 pages.
International Preliminary Report on Patentability dated Sep. 15, 2016, directed to International Application No. PCT/CA2015/050158; 5 pages.
International Search Report dated Dec. 13, 2016, directed to International Application No. PCT/CA2016/051023; 3 pages.
International Search Report dated May 14, 2015, directed to International Application PCT/CA2015/050158; 3 pages.
International Search Report dated May 31, 2016, directed International Application No. PCT/CA2016/050365; 4 pages.
Office Action dated Jun. 11, 2018, directed to JP Application 2016-555505; 11 pages.
Notice of Allowance dated Jan. 24, 2020, directed to JP Application No. 2018-192776; 7 pages.
Notice of Allowance dated Oct. 4, 2019, directed to JP Application No. 2017-551311; 7 pages.
Decision to Grant a Patent dated Jan. 7, 2019, directed to JP Application No. 2016-555473; 6 pages.
Notification of Reasons for Refusal dated Dec. 13, 2019, directed to JP Application No. 2018-510932; 10 pages.
Final Rejection dated Jul. 3, 2020, directed to JP Application No. 2018-510932; 6 pages.
Notification of Reasons for Refusal dated Jul. 8, 2019, directed to JP Application No. 2018-192776; 10 pages.
Notification of Reasons for Refusal dated Mar. 11, 2019, directed to JP Application No. 2018-510932; 10 pages.
Notification of Reasons for Refusal dated Nov. 9, 2018, directed to JP Application No. 2017-551311; 14 pages.
Office Action dated Apr. 20, 2018, directed to JP Application No. 2016-555473; 9 pages.
Office Action dated Aug. 25, 2017, directed to JP Application No. 2016-555473; 11 pages.
Office Action dated Jul. 14, 2017, directed to JP Application No. 2016-555505; 13 pages.
Office Action dated Nov. 25, 2019, directed to JP Application No. 2019-019015; 10 pages.
Search Report dated Nov. 11, 2019, directed to JP Application No. 2019-019015; 17 pages.
Notice of Reasons for Refusal dated May 25, 2020, directed to JP Application No. 2019-019015; 8 pages.
Decision to Grant a Patent dated Jul. 31, 2020, directed to JP Application No. 2019-019015; 6 pages.
Notice of Reasons for Refusal dated Oct. 8, 2021, directed to JP Application No. 2020-179950; 12 pages.
Notice of Reasons for Refusal dated Aug. 8, 2022, directed to JP Application No. 2020-179950; 8 pages.
Decision of Refusal dated Jul. 24, 2018, directed to KR Application No. 10-2016-7027305; 7 pages.
Notice of Allowance for Patent dated Nov. 12, 2018, directed to KR Application No. 10-2016-7026942; 3 pages.
Notice of Allowance for Patent dated Sep. 20, 2019, directed to KR Application No. 10-2016-7027305; 3 pages.
Office Action dated Dec. 13, 2017, directed to KR Application No. 2016-7026942; 12 pages.
Office Action dated Nov. 23, 2018, directed to KR Application No. 2016-7027305; 13 pages.
Office Action dated Sep. 15, 2017, directed to KR Application No. 2016-7027305; 14 pages.
Reichman, J. (Jun. 1998). "Handbook of Optical Filters for Fluorescence Microscopy," pp. 2-30, G1-G5, (37 pages) located at: http://www.cyto.purdue.edu/cdroms/micro1/7_spon/chroma/handbk3.pdf, last visited on Jan. 31, 2020.
U.S. Final Office Action dated Apr. 30, 2020, directed to U.S. Appl. No. 14/636,658; 22 pages.
U.S. Advisory Action dated Nov. 1, 2017, directed to U.S. Appl. No. 14/636,448; 4 pages.
U.S. Final Office Action dated Apr. 4, 2019, directed to U.S. Appl. No. 15/251,154; 20 pages.
U.S. Final Office Action dated Aug. 15, 2018, directed to U.S. Appl. No. 14/636,448; 7 pages.
U.S. Final Office Action dated Aug. 2, 2017, directed to U.S. Appl. No. 14/636,448; 6 pages.
U.S. Final Office Action dated Dec. 20, 2019, directed to U.S. Appl. No. 14/636,658; 25 pages.
U.S. Final Office Action dated Oct. 18, 2018, directed to U.S. Appl. No. 14/636,658; 26 pages.
U.S. Final Office Action dated Sep. 1, 2017, directed to U.S. Appl. No. 14/636,658; 17 pages.
U.S. Non-Final Office Action dated Dec. 14, 2017, directed to U.S. Appl. No. 14/636,448; 8 pages.
U.S. Non-Final Office Action dated Dec. 2, 2019, directed to U.S. Appl. No. 15/251,154; 14 pages.
U.S. Non-Final Office Action dated Feb. 8, 2018, directed to U.S. Appl. No. 14/636,658; 21 pages.
U.S. Non-Final Office Action dated Jun. 27, 2017, directed to U.S. Appl. No. 15/083,357; 13 pages.
U.S. Non-Final Office Action dated May 8, 2019, directed to U.S. Appl. No. 14/636,658; 22 pages.
U.S. Non-Final Office Action dated Nov. 4, 2016, directed to U.S. Appl. No. 14/636,448; 8 pages.
U.S. Non-Final Office Action dated Oct. 21, 2016, directed to U.S. Appl. No. 14/636,658; 12 pages.
U.S. Non-Final Office Action dated Sep. 21, 2018, directed to U.S. Appl. No. 15/251,154; 31 pages.
U.S. Non-Final Office Action dated Sep. 5, 2019, directed to U.S. Appl. No. 14/636,448; 11 pages.
Moore, Examiner's Answer dated Apr. 16, 2020, directed to U.S. Appl. No. 14/636,448; 13 pages.
Moore, Decision on Appeal dated Sep. 20, 2021, directed to U.S. Appl. No. 14/636,448; 11 pages.
Moore, U.S. Notice of Allowance and Fee(s) Due dated Dec. 21, 2021, directed to U.S. Appl. No. 14/636,448; 8 pages.
Moore et al., U.S. Office Action dated Sep. 29, 2022, directed to U.S. Appl. No. 17/178,082; 19 pages.
U.S. Notice of Allowance dated Feb. 1, 2018, directed to U.S. Appl. No. 15/083,357; 8 pages.
U.S. Restriction Requirement dated May 2, 2016, directed to U.S. Appl. No. 14/636,658; 9 pages.
Moore. U.S. Notice of Allowance and Fee(s) Due dated Nov. 16, 2020, directed to U.S. Appl. No. 14/636,658; 9 pages.
Written Opinion of the International Searching Authority dated Dec. 13, 2016, directed to International Application No. PCT/CA2016/051023; 4 pages.
Written Opinion of the International Searching Authority dated May 13, 2015, directed to International Application No. PCT/CA2015/050162; 5 pages.
Written Opinion of the International Searching Authority dated May 14, 2015, directed to International Application No. PCT/CA2015/050158; 3 pages.
Written Opinion of the International Searching Authority dated May 31, 2016, directed to International Application No. PCT/CA2016/050365; 5 pages.

\* cited by examiner

RELAY LENS SYSTEM FOR BROADBAND IMAGING

CROSS-REFERENCE TO RELATED APPLICATIONS

This application is a continuation of U.S. patent application Ser. No. 14/636,448, filed Mar. 3, 2015, which claims the benefit of U.S. Provisional Application No. 61/947,776, filed Mar. 4, 2014, and U.S. Provisional Application No. 62/084,292, filed Nov. 25, 2014, the entire contents of each of which are incorporated by reference herein.

TECHNICAL FIELD

The present disclosure relates generally to the field of optical lens systems. More specifically, the disclosure relates to rod-type relay lens systems for use in broadband imaging.

BACKGROUND

Medical endoscopes are used to view internal body organs and tissue through small openings created in and through the body wall or skin or by way of existing openings or orifices. For example, fluorescence endoscopy is an endoscopic examination method in which fluorescent dye is administered to patients and excited with light having a specific excitation wavelength. The excited fluorescent dye emits light of a specific emission wavelength, which is longer than the excitation wavelength, so that visualization of tissue and/or vessels containing the dye can be enhanced relative to conventional white-light endoscopy.

SUMMARY

One or more embodiments are directed to an optical system, including a first relay rod of a first material, a second relay rod of a second material, different from the first material, and a lens between the first and second relay rods.

The first and second materials may be selected to reduce the wavefront error across the field of view of the optical system as compared with using a same material for both the first and second relay rods.

The first and second relay rods may have no optical power.

The first and second relay rods may have no optically powered surfaces.

The first and second relay rods may be geometrically symmetric to one another relative to a pupil or conjugate pupil of the optical system.

The lens may include a first relay objective and a second relay objective.

The first and second relay objectives may have a same design and material.

A pupil region of the system may be in air.

The optical system may include a third relay rod of a third material, a fourth relay rod of a fourth material, the fourth material being different from the third material; and a lens between the third and fourth relay rods.

The first and third materials are the same and the second and fourth materials may be the same.

The optical system may include a detector to detect light from 460 nm to 850 nm.

The optical system may be in an endoscope.

One or more embodiments are directed to a kit including a first relay rod of a first material, a second relay rod of a second material, different from the first material, and a lens to be inserted between the first and second relay rods.

The lens may include a first relay objective and a second relay objective.

The first and second relay objectives have a same design and material.

One or more embodiments are directed to a method of compensating for dispersion in a relay lens system, the method including providing a first relay rod of a first material, providing a second relay rod of a second material, different from the first material, and providing a lens between the first and second relay rods.

BRIEF DESCRIPTION OF THE DRAWINGS

Features will become apparent to those of skill in the art by describing in detail exemplary embodiments with reference to the attached drawings in which.

DETAILED DESCRIPTION

Figure 1A:
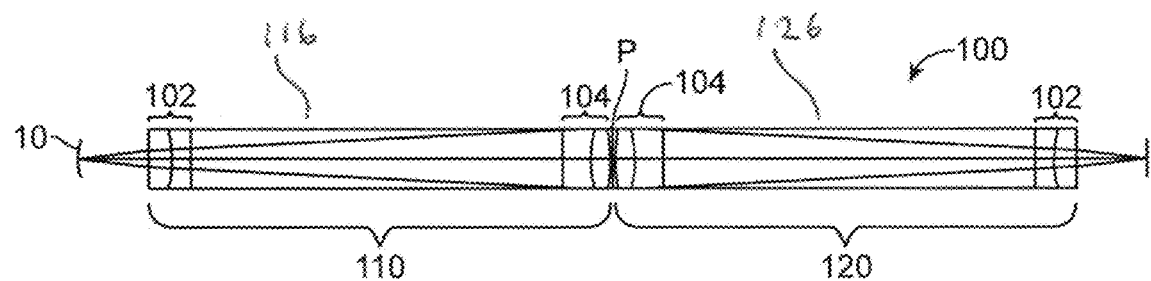
FIGS. 1A and 1B illustrate a relay pair according to an embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

Generally, corresponding or similar reference numbers will be used, when possible, throughout the drawings to refer to the same or corresponding parts.

Optical design requirements for endoscopes have changed with the introduction of new technologies, such as image sensors and solid state illumination. An endoscope designed for visual use only may be optimized for F, d, C light, which spans the region of 486 nm through to 656 nm. An endoscope designed for machine vision, where a camera will display an image on a monitor, may operate with illumination wavelengths extending further into the blue, for example to 460 nm. Additionally, there is demand to visualize tissue and body structures in other waveband regimes beyond that of visible bands, e.g., near infrared regions (700 nm to 900 nm) where tissue is maximally transparent to light and where dyes such as Indocyanine Green (ICG) fluoresce and are used as markers. Additionally, the resolution required of endoscopes has increased with the introduction of high definition (HD) video image sensors having smaller and more numerous pixels than earlier NTSC or PAL formats. In both diagnostic and therapeutic procedures where endoscopes are used, it is advantageous to provide guiding imagery and fluorescent markers. Accordingly, high resolution imaging is desired in the visible bands as well as in longer wavelength regions beyond that of human vision.

Imaging optical systems, including endoscopes, must be designed with the operational wavelengths in mind. The refractive properties of materials are such that light of different wavelengths will propagate along slightly different paths through an optical system, and arrive at slightly different image planes. In order to ensure that the image planes for different wavelengths are sufficiently close so as not to degrade image quality, the design of the system must take into consideration these refractive properties.

A system designed for use across a broadband of wavelengths, e.g., between 460 nm to 850 nm, may have one or more image sensors. If the system has two sensors, e.g., one for the visible region and one for the near infrared region, then the design of the system may consider separately the problems of image quality for the visible and image quality for the near infrared region, since each region will have its own corresponding sensor. If however, the system operates with a single image sensor, then the system must focus all light throughout its operational waveband onto one image plane. This latter condition is more difficult, but also offers more utility to the remainder of the design, as a single sensor maybe used.

A system designed for broadband use, for example visible and near infrared, and designed for single sensor operation, requires tight control over chromatic aberrations, such as axial color. Light of different wavelengths focus at different distances from the optics. Axial color arises from dispersion, i.e., the variation of refractive index versus wavelength in refractive materials. Sensitivity to dispersion increases as the f/# is faster.

Therefore, one or more embodiments is directed to providing a relay lens system that offsets the effect of dispersion as light propagates through the system, as discussed in detail below.

Figure 1B:
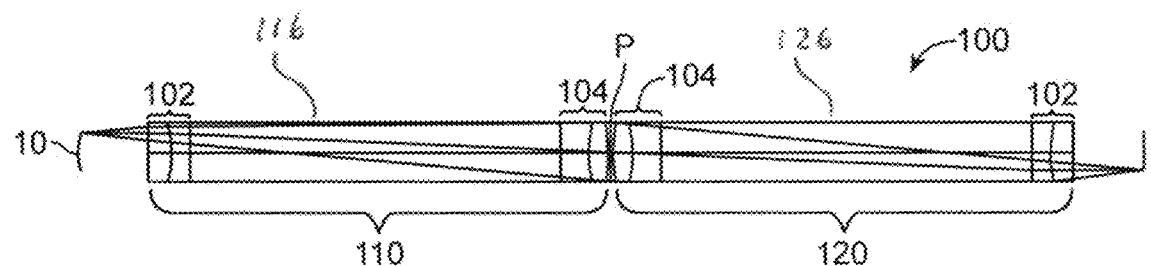
Figure 1C:
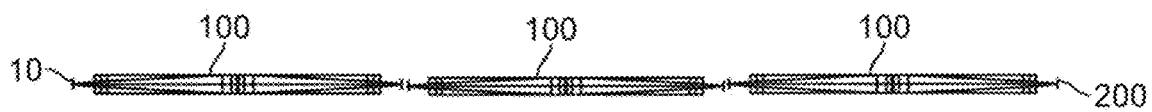
FIG. 1C illustrates a plurality of relay pairs.

FIGS. 1A and 1B illustrate an exemplary relay pair 100 for a broadband system using a single detector. FIG. 1A illustrates the on-axis beam and FIG. 1B illustrates the off-axis beam. FIG. 1C illustrates an odd number of relay pairs to produce an upright image at a detector 200. In particular, the image after an objective lens 10 in inverted, so any odd number of relay pairs, e.g., 1, 3, 5, 7, and so forth, will produce an upright image.

The relay pair includes a first relay rod lens assembly 110 and a second relay rod lens assembly 120. Each of the first and second relay rod lens assemblies 110, 120 includes a rod 116, 126, respectively, and a plurality of bonded lenses selected to provide color correction from a lower limit, e.g., 460 nm, to an upper limit, e.g., 850 nm. In particular, the bonded lenses may include a relay field lens 102 and a relay objective 104, here both shown as doublets.

Figure 2:
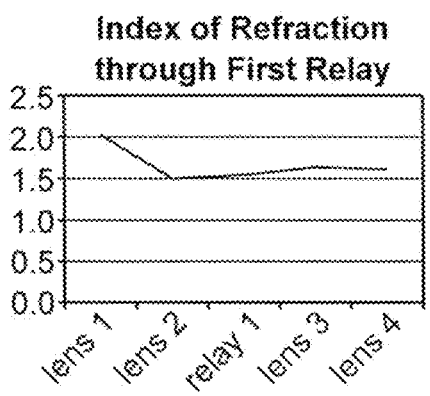
FIG. 2 illustrates how index and Abbe values interplay through a relay set.
Figure 2:
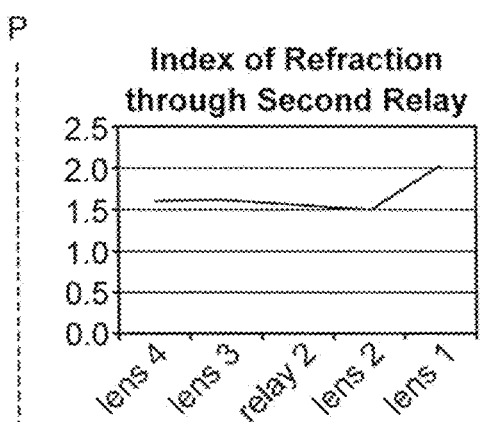
Figure 2:
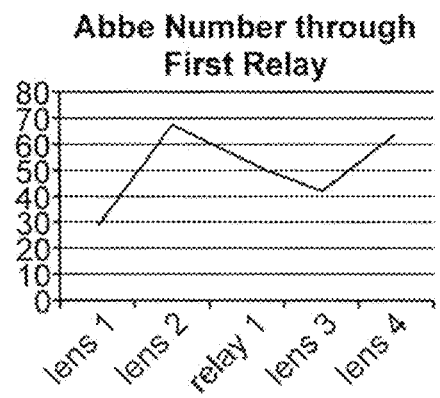
Figure 2:
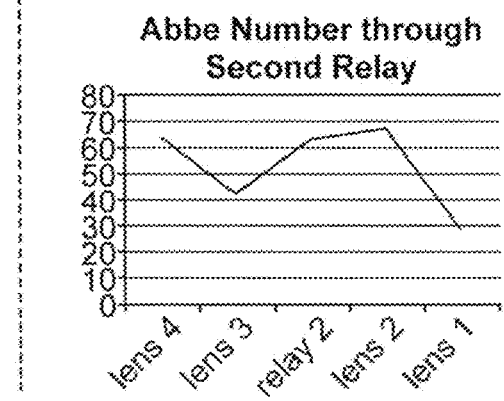

The rods 116, 126 are made of different materials that compensate for residual wavefront error in the relay pair 100 as illustrated in FIG. 2. The diffraction-limited relay pair in FIG. 2 illustrates refractive index symmetry about the pupil region P, and Abbe number asymmetry about the pupil region P.

The relay pair 100 operates with unit magnification. The bonded lenses of the relay rod lens assemblies 110 and 120 are symmetric or mirrored about a pupil (or aperture stop) 130 between the first and second relay rod assemblies 110, 120. In other words, the relay field lenses 102 and the relay objectives 104 are the same, i.e., the same material, the same prescription, and so forth, throughout the relay pair 100.

Although a design is optimized based on wavefront error and MTF performance, and although this process will offset some aberrations through constructive introduction of other aberrations, it may be helpful to explore the problem in traditional terms, such as may be found by considering the system in terms of Seidel errors. While typical, symmetrical design of the relay pair will correct for odd Seidel aberrations, e.g., coma, distortion, lateral chromatic aberration, and so forth, even Seidel aberrations, e.g., spherical, astigmatism, field curvature, axial chromatic, and so forth, are not corrected by such symmetry. Axial chromatic aberration is of particular concern as the wavelength bandwidth increases, while the image plane remains constrained to a single detector. Additional lenses or different lenses on different sides of the relay pupil may be used to correct for the dispersion, but this increases cost and complexity.

However, by using different materials for the relay rod in the first and second relay rod lens assemblies 110, 120 in accordance with an embodiment, the basic form of the relay pair 100 may be maintained. In other words, since the material of the relay rods introduce dispersion themselves, by selecting appropriate materials for the relay rods 116, 126 in the first and second relay rod lens assemblies 110, 120, the dispersion over the relay pair 100 may be compensated, while otherwise using the same elements throughout the relay pair 100. The relay rod carries no optical power, but instead is used to make the space between powered elements appear to have a shorter optical path distance, without using total internal reflection.

Thus, by treating the material of the relay rod as another degree of freedom, dispersion in the relay pair 100 may be altered, i.e., corrected, without modifying the basic form. The relay rod lens assemblies 110 and 120 will have nearly identical focal lengths in order to meet the required unit magnification. The first rod 116 and the second rod 126 are symmetrical to one another relative to the pupil. However, as noted above, the first rod 116 is made of a first glass type and the second rod 126 is made of a second glass type. The second glass type is different from the first glass type. In design, the first glass type and the second glass type are selected to reduce residual wavefront error within the optical system. Otherwise, the pair of relay and rod lens assembly is identically configured, e.g., identical lengths, identical lens elements, identical geometric form, and so forth, while using different rod materials.

Figure 3:
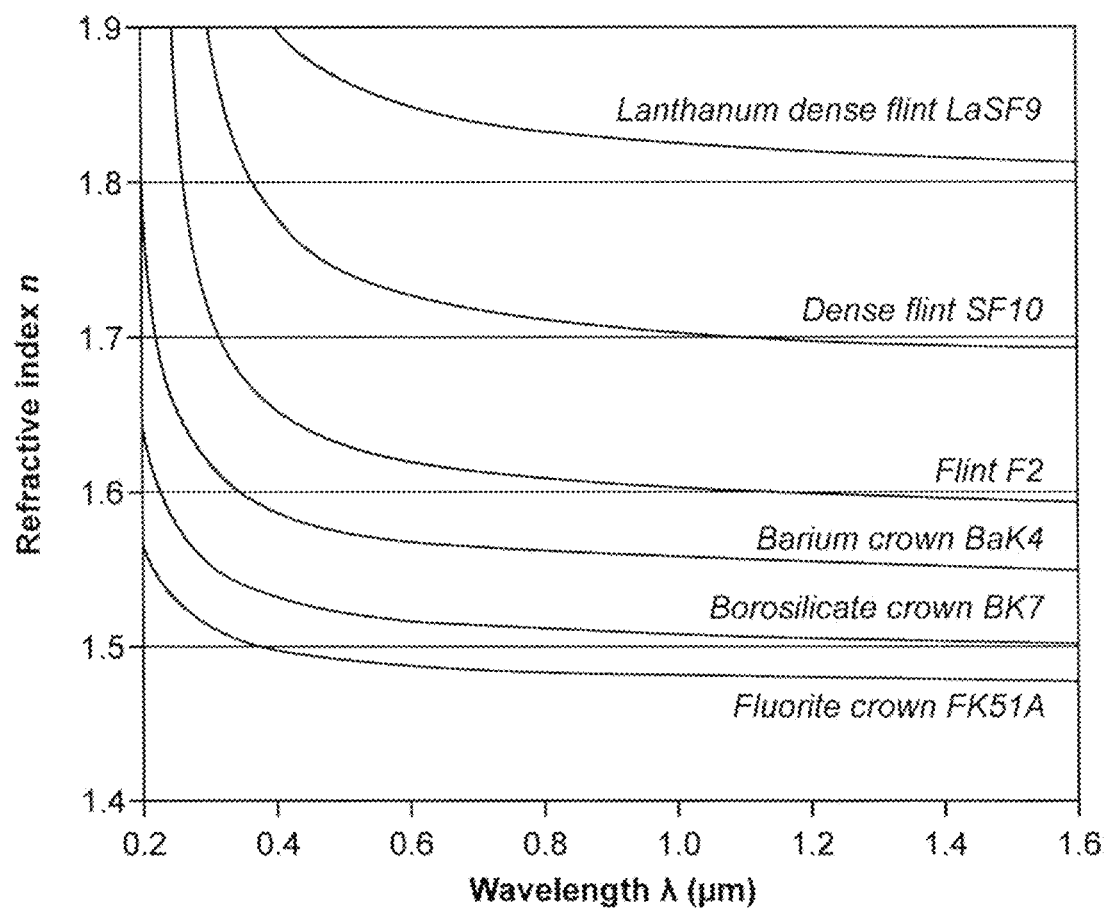
FIG. 3 is a graph of refractive index versus wavelength for exemplary glass types.
Figure 4:
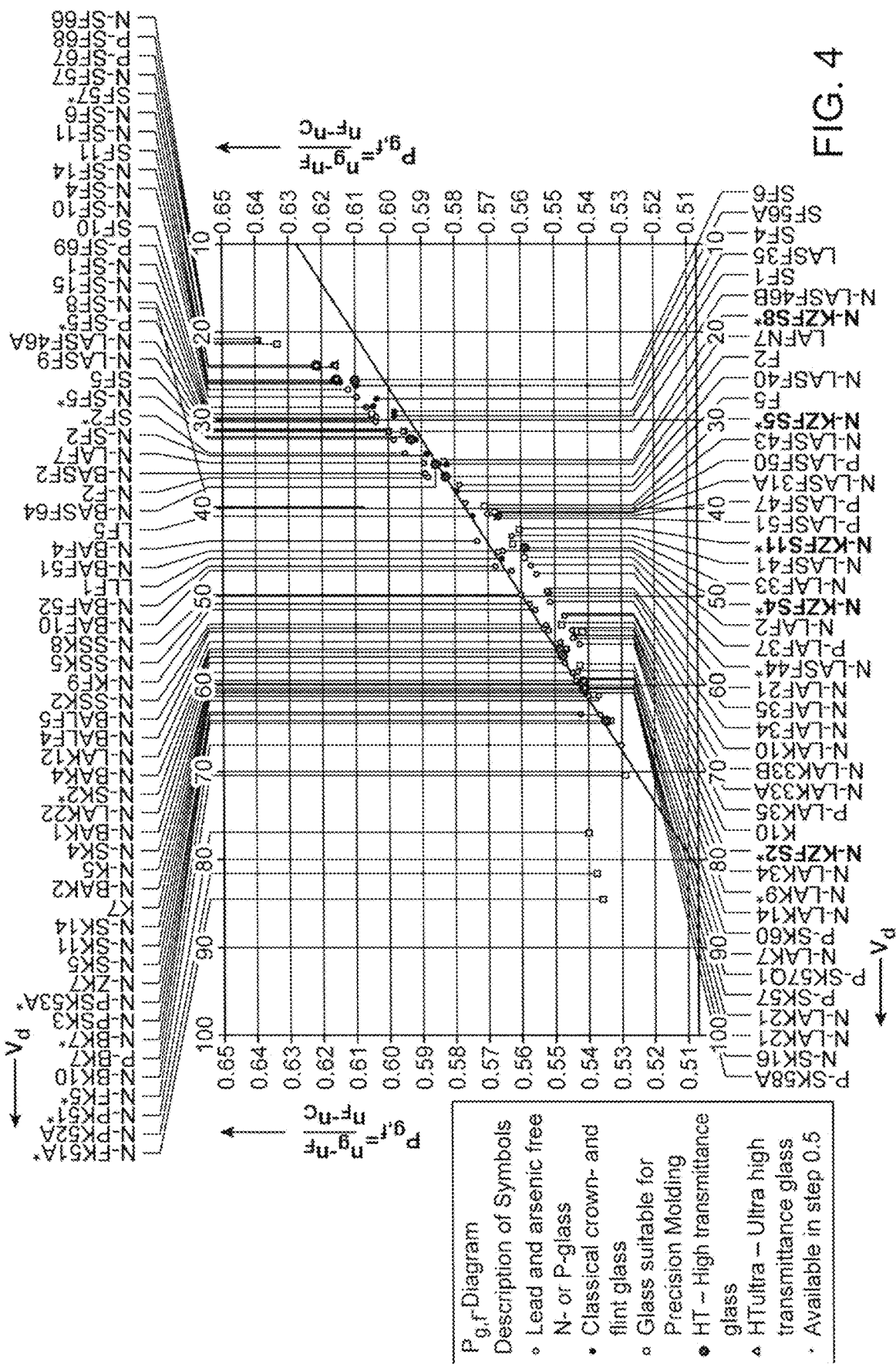
FIG. 4 is a graph illustrating partial dispersion versus inverse dispersion for various glass types.

Referring to FIG. 3, it can be seen that for any wavelength, different materials have different local tangents (derivatives). Thus, glass materials not only exhibit different aggregate dispersion (different inverse Abbe numbers) but also exhibit different partial dispersion, which is a measure of dispersion over a subset of the bandwidth. FIG. 4 illustrates how partial dispersion ($P_{g,F}$) varies with inverse dispersion (Abbe number or $V_d$) for SCHOTT®'s optical glass assortment.

Figure 5:
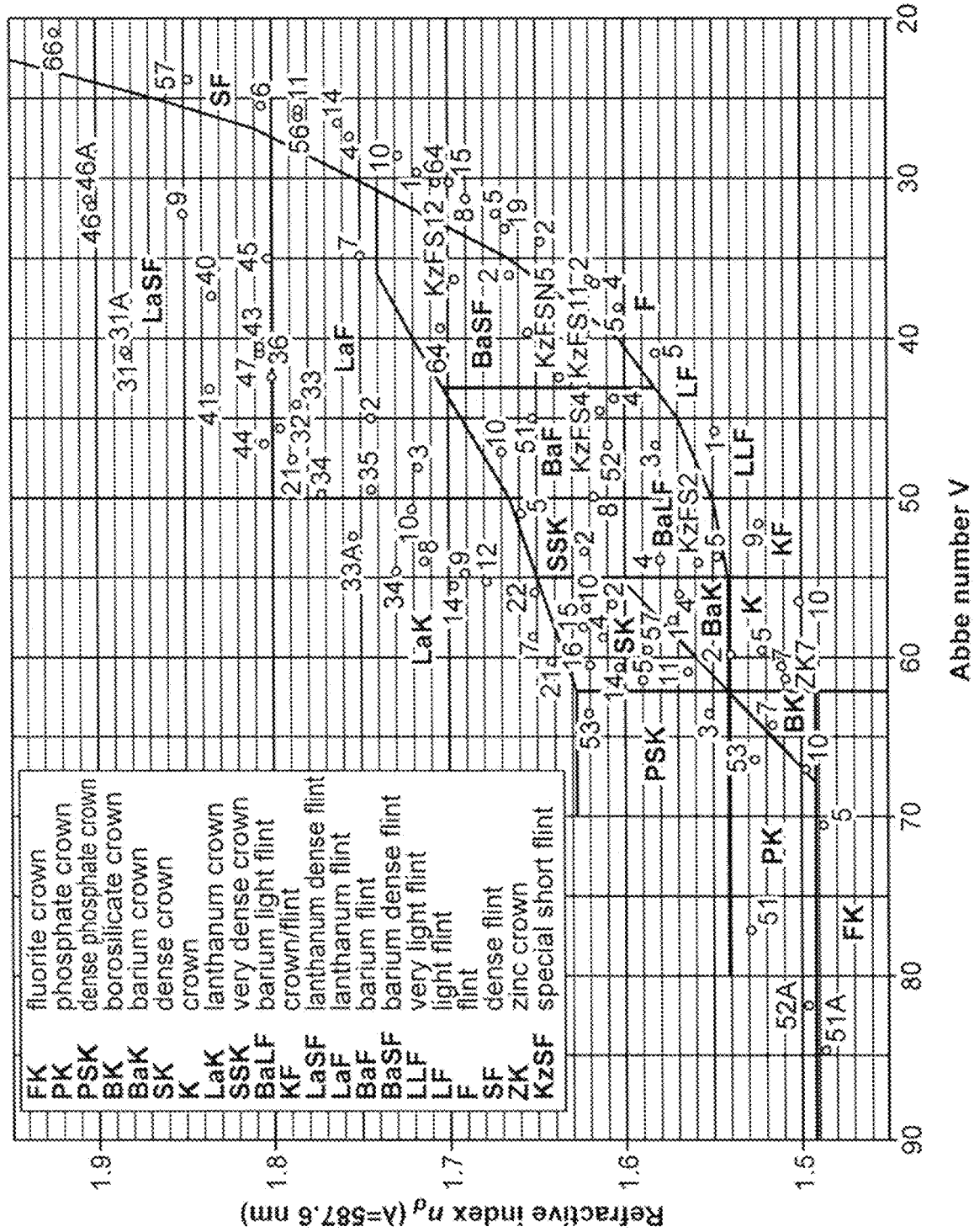
FIG. 5 is graph illustrating refractive index versus Abbe number for exemplary glasses.

Relay rod glass material is selected first for its transmission properties; a designer may build a design-specific list of materials ranked according to transmission, then draw upon the top candidates for their remainder attributes (such as index, dispersion, thermal coefficient, etc). In general, optical glasses that are reasonably well suited for use in relay rods tend to occur at abbe numbers between 35 and 65, and indices of refraction between 1.5 and 1.65 (refer to the plot of refractive index versus Abbe number of FIG. 5, in which some suitable glasses made by SCHOTT® with Abbe numbers between 50 and 65 include, e.g., N-PSK3, N-BALF5, N-SK2, N-BAK2, N-K5 and N-KF9). Glasses that will form the outer elements may be then selected based on other design requirements, such as their thermal coefficients relative to their neighbor glass on the other side of a lens bond.

Optimization for minimum wavefront error across all field positions will drive the form to be symmetric about the pupil in regard to index of refraction, and asymmetric about the pupil in regard to Abbe number (or inverse dispersion). An example of a diffraction-limited solution is illustrated in FIG. 2. The outer elements, i.e., the relay objectives and field lenses will be the same on both sides of the relay pupil. The focal lengths for each relay rod lens assembly are nearly identical, but the partial dispersions of the relay rod lens assemblies due to the different rod materials have compensatory effects on residual wavefront error.

Figure 6A:
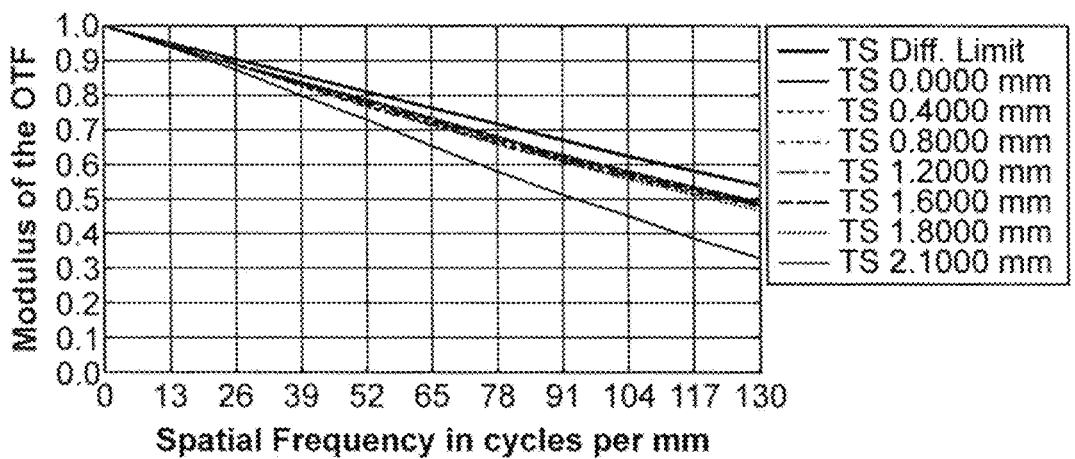
FIGS. 6A to 6C illustrate plots of MTF versus spatial frequency for comparative examples and an example according to an embodiment.
Figure 6B:
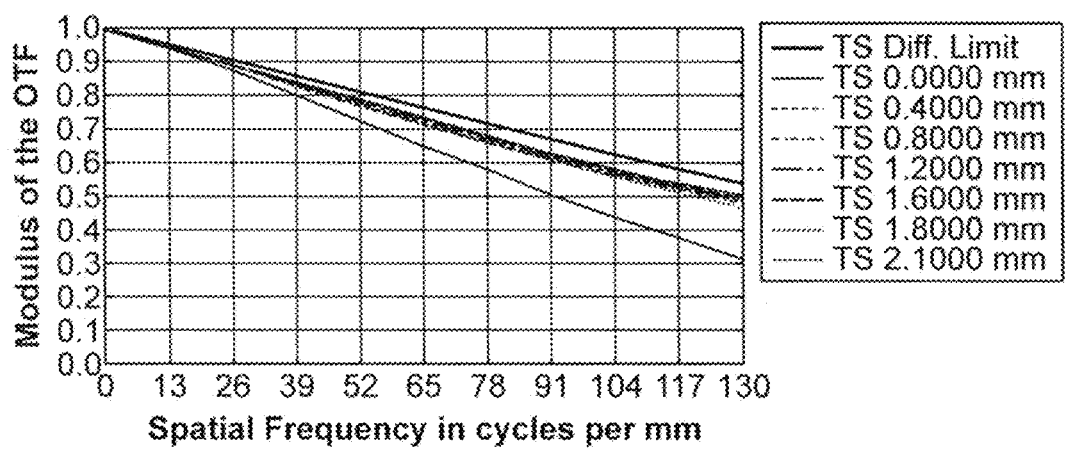
Figure 6C:
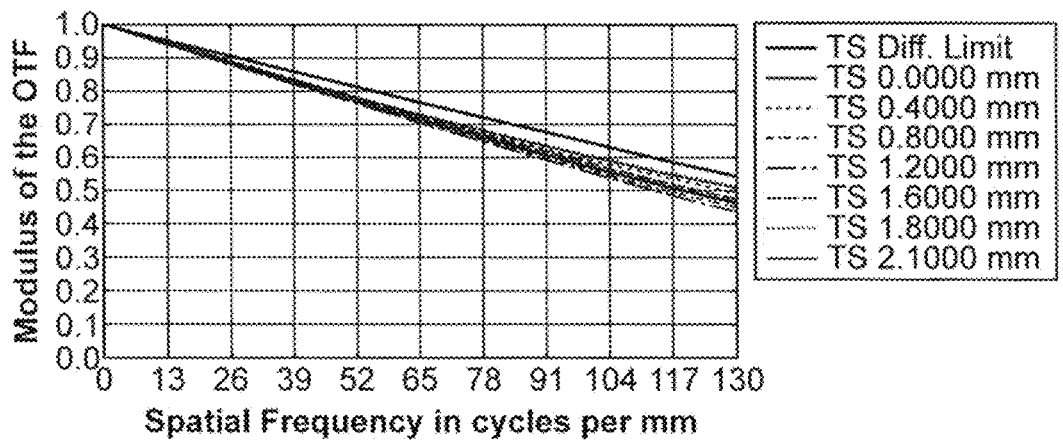

FIGS. 6A to 6C illustrate dispersion in a comparative example and an example according to an embodiment. FIG. 6A shows a plot of the modulus of the optical transfer function (OTF) (MTF) versus spatial frequency in cycles per mm for an F/4.5 relay in which the same material, here N-PSK3, is used for both relay rods in a relay system for a 30 cm visible-near infrared endoscope having three relay pairs. FIG. 6B shows a plot of MTF versus spatial frequency in which elements of the same relay system as used for FIG. 6A are used, except the same material for the relay rods is N-BALF5. FIG. 6C shows a plot of MTF versus spatial frequency in which elements of the same relay system as used for FIG. 6A are used, except different materials are used for the relay rods on opposite sides of the relay pupil. For example, a first material, here N-PSK3, is used for the first relay rod, and a second material, here N-BALF5, is used for the second material. The comparing FIGS. 6A to 6C, the MTF for the transverse off-axis ray is significantly improved by use two different materials for the relay rods.

By way of summation and review, endoscopes typically include a long, thin, rigid or semi-rigid optical cylinder that is mounted on or to a viewing mechanism or imager. When the endoscope is inserted and positioned for use, an image of the object being viewed is formed by an objective lens at the inserted or distal end of the endoscope. The image passes through a relay lens system, comprising of one or more sets of relay lenses, along the cylinder to a viewer comprising an eyepiece or viewing lens or a video camera or imager at the viewing or proximal end of the endoscope.

A relay lens system will reconstruct the image formed at the objective lens one or more times, depending on the number of relays used. A single relay will form one image. Additional relays may be used to form additional images. The purpose of these elements is not to produce many images, but rather to carry the image field to another position. Endoscopes are narrow in order to reduce the size of an incision. Endoscopes are long because the object under study may be deep within the body. The image formed by the objective lens at the distal end is relayed along the length of the endoscope to the proximal end by the relay lens system.

When used in endoscopes, the relay lenses may be very narrow, e.g., less than 6.5 mm in diameter and approximately 20 mm to 50 mm long. Most endoscopes require three or more sets of relay lenses for proper operation. The number of lenses generally depends on the length and specific requirements of the particular endoscope and/or the application for which it is intended. Because the objective and each relay set is producing an image with unit magnification which is turned upside down, and because a standard endoscope should produce an upright image, usually an odd number of relay lenses are used so that the image produced by the optical system at the ocular or at the detector, is upright.

For good image quality, the optical system of an endoscope should be well corrected for the major lens aberrations. A relay lens typically operates with unit magnification with lenses configured to be symmetric about the relay's internal stop plane, i.e., the pupil within the relay. This set of conditions will result in the odd Seidel aberrations formed by the lenses before the relay's pupil to be cancelled out by the lenses after the relay's pupil. However, the even Seidel aberrations are not corrected. As noted above, these even Seidel aberrations may become more problematic as an operational waveband over which the optical system is to perform increases.

According to an embodiment discussed above, using different materials for relay rods on opposite sides of the relay pupil may allow dispersion to be compensated without changing the basic form of the relay. In other words, by using different rod materials on opposite sides of the relay pupil, other elements, e.g., objectives and field lenses, on opposite sides of the relay pupil may be identical, such that the pair of relay rod lens assemblies are otherwise identically configured, e.g., identical lengths, identical lens elements, identical geometric form, and so forth, while using different rod materials.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims. For example, while specific examples have been directed to endoscopes, embodiments may be used with other imaging system with similar waveband and single detector requirements, e.g., borescopes.

What is claimed is:

1. An optical system, comprising:
   a first relay rod of a first material, the first relay rod having no optical power;
   a second relay rod of a second material, different from the first material, wherein the first and second materials are selected to reduce the wavefront error across the field of view of the optical system as compared with using a same material for both the first and second relay rods, the second relay rod having no optical power, wherein the first and second relay rods are geometrically symmetric to one another relative to a pupil or conjugate pupil of the optical system, the first and second relay rods having a same length; and
   a lens between the first and second relay rods.

2. The optical system of claim 1, wherein the lens includes a first relay objective and a second relay objective.

3. The optical system of claim 1, wherein a pupil region of the system is in air.

4. The optical system of claim 1, further comprising:
   a third relay rod of a third material;
   a fourth relay rod of a fourth material, the fourth material being different from the third material; and
   a lens between the third and fourth relay rods.

5. The optical system of claim 4, wherein the first and third materials are the same and the second and fourth materials are the same.

6. The optical system of claim 1, further comprising a detector to detect light from 460 nm to 850 nm.

7. The optical system of claim 1, wherein the first and second relay rods and the lens has refractive index symmetry and Abbe number asymmetry about a pupil region.

8. An endoscope including the optical system of claim 1.

9. A kit, comprising:
a first relay rod of a first material, the first relay rod having no optical power;
a second relay rod of a second material, different from the first material, wherein the first and second materials are selected to reduce the wavefront error across the field of view of the optical system as compared with using a same material for both the first and second relay rods, the second relay rod having no optical power, wherein the first and second relay rods are geometrically symmetric to one another relative to a pupil or conjugate pupil of the optical system, the first and second relay rods having a same length; and
a lens to be inserted between the first and second relay rods.

10. The kit of claim 9, wherein the lens includes a first relay objective and a second relay objective.

11. The kit of claim 9, wherein the first and second relay rods and the lens has refractive index symmetry and Abbe number asymmetry about a pupil region.

12. A method of compensating for dispersion in a relay lens system, the method comprising:
providing a first relay rod of a first material, the first relay rod having no optical power;
providing a second relay rod of a second material, different from the first material, wherein the first and second materials are selected to reduce the wavefront error across the field of view of the optical system as compared with using a same material for both the first and second relay rods, the second relay rod having no optical power, wherein the first and second relay rods are geometrically symmetric to one another relative to a pupil or conjugate pupil of the optical system, the first and second relay rods having a same length; and
providing a lens between the first and second relay rods.

13. The method of claim 12, wherein the lens includes a first relay objective and a second relay objective.

14. The method of claim 12, wherein the first and second relay rods and the lens has refractive index symmetry and Abbe number asymmetry about a pupil region.

* * * * *